(12) United States Patent
Rohaly et al.

(10) Patent No.: US 9,418,474 B2
(45) Date of Patent: Aug. 16, 2016

(54) THREE-DIMENSIONAL MODEL REFINEMENT

(75) Inventors: Janos Rohaly, Acton, MA (US); Ilya A. Kriveshko, Littleton, MA (US); Dmitriy A. Dedkov, Everett, MA (US)

(73) Assignee: 3M INNOVATIVE PROPERTIES COMPANY, Saint Paul, MN (US)

( * ) Notice: Subject to any disclaimer, the term of this patent is extended or adjusted under 35 U.S.C. 154(b) by 1544 days.

(21) Appl. No.: 12/811,237

(22) PCT Filed: Jan. 4, 2009

(86) PCT No.: PCT/US2009/030065
§ 371 (c)(1),
(2), (4) Date: Sep. 22, 2010

(87) PCT Pub. No.: WO2009/089126
PCT Pub. Date: Jul. 16, 2009

(65) Prior Publication Data
US 2011/0043613 A1    Feb. 24, 2011

Related U.S. Application Data

(60) Provisional application No. 61/019,159, filed on Jan. 4, 2008.

(51) Int. Cl.
*H04N 13/02*    (2006.01)
*G06T 17/00*    (2006.01)
*A61C 13/00*    (2006.01)
*G06K 9/00*    (2006.01)

(52) U.S. Cl.
CPC ............. *G06T 17/00* (2013.01); *A61C 13/0004* (2013.01); *G06K 9/00201* (2013.01); *G06K 9/00214* (2013.01); *H04N 13/0221* (2013.01); *G06T 2207/10012* (2013.01); *G06T 2210/41* (2013.01)

(58) Field of Classification Search
USPC ............................... 348/42, 50; 382/118, 154
IPC ......................................................... H04N 13/02
See application file for complete search history.

(56) References Cited

U.S. PATENT DOCUMENTS

| 6,219,437 B1 | 4/2001 | Baldur |
| 6,973,204 B2 | 12/2005 | Adachi |
| 7,085,323 B2 | 8/2006 | Hong |
| 7,372,642 B2 | 5/2008 | Rohaly et al. |

(Continued)

FOREIGN PATENT DOCUMENTS

KR    2007-0039641    4/2007

OTHER PUBLICATIONS

Dorst, "First Order Propagation of the Procrustes Method for 3D Attitude Estimation", IEEE Transactions on Pattern Analysis and Machine Intelligence, vol. 27, No. 2, Feb. 2005, pp. 221-229.

(Continued)

*Primary Examiner* — Jay Patel
*Assistant Examiner* — Neil Mikeska

(57) ABSTRACT

A three-dimensional measurement is refined by warping two-dimensional images of an object from offset camera positions according to a three-dimensional model of the object, and applying any resulting discrepancies to refine the three-dimensional model, or to refine one of a number of three-dimensional measurements used to create the three-dimensional model.

22 Claims, 8 Drawing Sheets

(56) References Cited

U.S. PATENT DOCUMENTS

| | | |
|---|---|---|
| 7,508,430 B1 | 3/2009 | Oten et al. |
| 7,605,817 B2 | 10/2009 | Zhang et al. |
| 2001/0016063 A1 | 8/2001 | Albeck et al. |
| 2001/0033326 A1* | 10/2001 | Goldstein et al. ............... 348/42 |
| 2002/0136444 A1 | 9/2002 | Brown et al. |
| 2004/0051783 A1 | 3/2004 | Chellappa et al. |
| 2004/0197728 A1 | 10/2004 | Abolfathi et al. |
| 2005/0089213 A1* | 4/2005 | Geng ............................. 382/154 |
| 2005/0089214 A1 | 4/2005 | Rubbert et al. |
| 2005/0089822 A1 | 4/2005 | Geng |
| 2005/0285874 A1 | 12/2005 | Zitnick, II et al. |
| 2006/0154198 A1* | 7/2006 | Durbin et al. ................... 433/29 |
| 2006/0204076 A1 | 9/2006 | Avanish et al. |
| 2007/0031064 A1 | 2/2007 | Zhao et al. |
| 2007/0103460 A1 | 5/2007 | Zhang et al. |
| 2007/0110338 A1 | 5/2007 | Snavely et al. |
| 2007/0127813 A1 | 6/2007 | Shah |
| 2007/0141534 A1 | 6/2007 | Wen |
| 2007/0172101 A1 | 7/2007 | Kriveshko et al. |
| 2007/0172112 A1 | 7/2007 | Paley et al. |

OTHER PUBLICATIONS

Zhang, "Hierarchical Block-Based Disparity Estimation Using Mean Absolute Difference and Dynamic Programming", Proc. of the Int. Workshop on Very Low Bitrate Video Coding, pp. 114, 118, Athens Greece, Oct. 11-12, 2001.

Kriveshko et al., U.S. Appl. No. 12/811,268, filed Jun. 30, 2010.

Rohaly et al., U.S. Appl. No. 12/811,236, filed Sep. 22, 2010.

Zhang et al., U.S. Appl. No. 12/811,239, filed Sep. 22, 2010.

Zang et al., U.S. Appl. No. 12/811,242, filed Jun. 30, 2010.

Triggs et al., "Bundle adjustment—a modern synthesis" Vision algorithms: theory and practice (2000) pp. 153-177.

* cited by examiner

THREE-DIMENSIONAL MODEL REFINEMENT

CROSS REFERENCE TO RELATED APPLICATIONS

This application is a national stage filing under 35 U.S.C. 371 of PCT/US2009/030065, filed Jan. 4, 2009, which claims priority to U.S. Provisional Application No. 61/019,159, filed Jan. 4, 2008, the disclosure of which is incorporated by reference in their entirety herein.

FIELD OF INVENTION

This invention relates generally to three-dimensional imaging and more specifically to refinement of three dimensional models reconstructed from a sequence of three-dimensional measurements captured along a camera path.

BACKGROUND

In one technique for three-dimensional image reconstruction, a number of images or image sets of an object are captured with a camera that travels in a path over the surface of the object. Information from this image catalogue can then be used to reconstruct a three-dimensional model of the object based upon each camera position and three-dimensional measurement captured along the path. While individual measurements from the camera can contain noise from a variety of sources, the resulting three-dimensional model tends to smooth out this noise to recover three-dimensional data points more accurate than the individual measurements.

There remains a need for post-processing techniques to refine individual three-dimensional measurements based upon the full data set available for a completed three-dimensional scan.

SUMMARY

A three-dimensional measurement is refined by warping two-dimensional images of an object from offset camera positions according to a three-dimensional model of the object, and applying any resulting discrepancies to refine the three-dimensional model, or to refine one of a number of three-dimensional measurements used to create the three-dimensional model.

In one aspect, a method of refining a three-dimensional model described herein includes providing a three-dimensional model of an object; obtaining a first two-dimensional image of the object from a first camera pose; obtaining a second two-dimensional image of the object from a second camera pose, wherein the second two-dimensional image includes a common portion of a surface of the object with the first two-dimensional image; deforming the first two-dimensional image based upon a spatial relationship of the first camera pose, the second camera pose, and the three-dimensional model to obtain an expected image from the second camera pose based upon the first camera pose; comparing the second two-dimensional image to the expected image to identify one or more discrepancies; and correcting the three-dimensional model based upon the one or more discrepancies.

The first camera pose and the second camera pose may be a position and an orientation of a single camera in two dependent positions. The first camera pose and the second camera pose may be a position and an orientation of two offset channels of a multi-aperture camera. The first camera pose and the second camera pose may be a position and an orientation of a single camera in two independent positions. A relationship between the first camera pose and the second camera pose may be calculated based upon a three-dimensional measurement of the surface of the object from each of the first camera pose and the second camera pose. The method may include deriving the three-dimensional model from a plurality of three-dimensional measurements of the surface of the object from a plurality of camera poses including the first camera pose and the second camera pose. The method may include applying the one or more discrepancies to directly refine the three-dimensional model. The method may include applying the one or more discrepancies to refine a three-dimensional measurement from one or more of the first camera pose and the second camera pose to provide a refined measurement. The method may include refining a camera path calculation for a camera path used to create the three-dimensional model using the refined measurement to provide a refined camera path. The method may include using the refined camera path and the refined measurement to refine the three-dimensional model. The three-dimensional model may be a point cloud or a polygonal mesh. The object may be human dentition. The second camera pose may correspond to a center channel of a multi-aperture camera system, the center channel providing a conventional two-dimensional image of the object. The method may include obtaining a third two-dimensional image of the object from a third camera pose corresponding to a second side channel of the multi-aperture system and deforming the third two-dimensional image to an expected image for the center channel for use in further refining the three-dimensional measurement from the multi-aperture camera system.

In another aspect, computer program product for refining a three-dimensional model of an object described herein includes computer executable code embodied on a computer readable medium that, when executing on one or more computing devices, performs the steps of providing a three-dimensional model of an object; obtaining a first two-dimensional image of the object from a first camera pose; obtaining a second two-dimensional image of the object from a second camera pose, wherein the second two-dimensional image includes a common portion of a surface of the object with the first two-dimensional image; deforming the first two-dimensional image based upon a spatial relationship of the first camera pose, the second camera pose, and the three-dimensional model to obtain an expected image from the second camera pose based upon the first camera pose; comparing the second two-dimensional image to the expected image to identify one or more discrepancies; and correcting the three-dimensional model based upon the one or more discrepancies.

The first camera pose and the second camera pose may be a position and an orientation of a single camera in two dependent positions. The first camera pose and the second camera pose may be a position and an orientation of two offset channels of a multi-aperture camera. The first camera pose and the second camera pose may be a position and an orientation of a single camera in two independent positions. A relationship between the first camera pose and the second camera pose may be calculated based upon a three-dimensional measurement of the surface of the object from each of the first camera pose and the second camera pose. The computer program produce may include code for performing the step of deriving the three-dimensional model from a plurality of three-dimensional measurements of the surface of the object from a plurality of camera poses including the first camera pose and the second camera pose. The computer program produce may include code for performing the step of applying the one or more discrepancies to directly refine the three-dimensional model. The computer program produce may include code for performing the step of applying the one or more discrepancies to refine a three-dimensional measurement from one or more of the first camera pose and the second camera pose to provide a refined measurement. The computer program produce may include code for performing the step of refining a camera path calculation for a camera path used to create the three-dimensional model using the refined measurement to provide a refined camera path. The computer program produce may include code for performing the step of using the refined camera path and the refined measurement to refine the three-dimensional model. The three-dimensional model may be a point cloud or a polygonal mesh. The object may be human dentition. The second camera pose may correspond to a center channel of a multi-aperture camera system, the center channel providing a conventional two-dimensional image of the object. The computer program product may include code for performing the steps of obtaining a third two-dimensional image of the object from a third camera pose corresponding to a second side channel of the multi-aperture system and deforming the third two-dimensional image to an expected image for the center channel for use in further refining the three-dimensional measurement from the multi-aperture camera system.

BRIEF DESCRIPTION OF THE DRAWINGS

The invention and the following detailed description of certain embodiments thereof may be understood by reference to the following figures.

DETAILED DESCRIPTION

Figure 1:
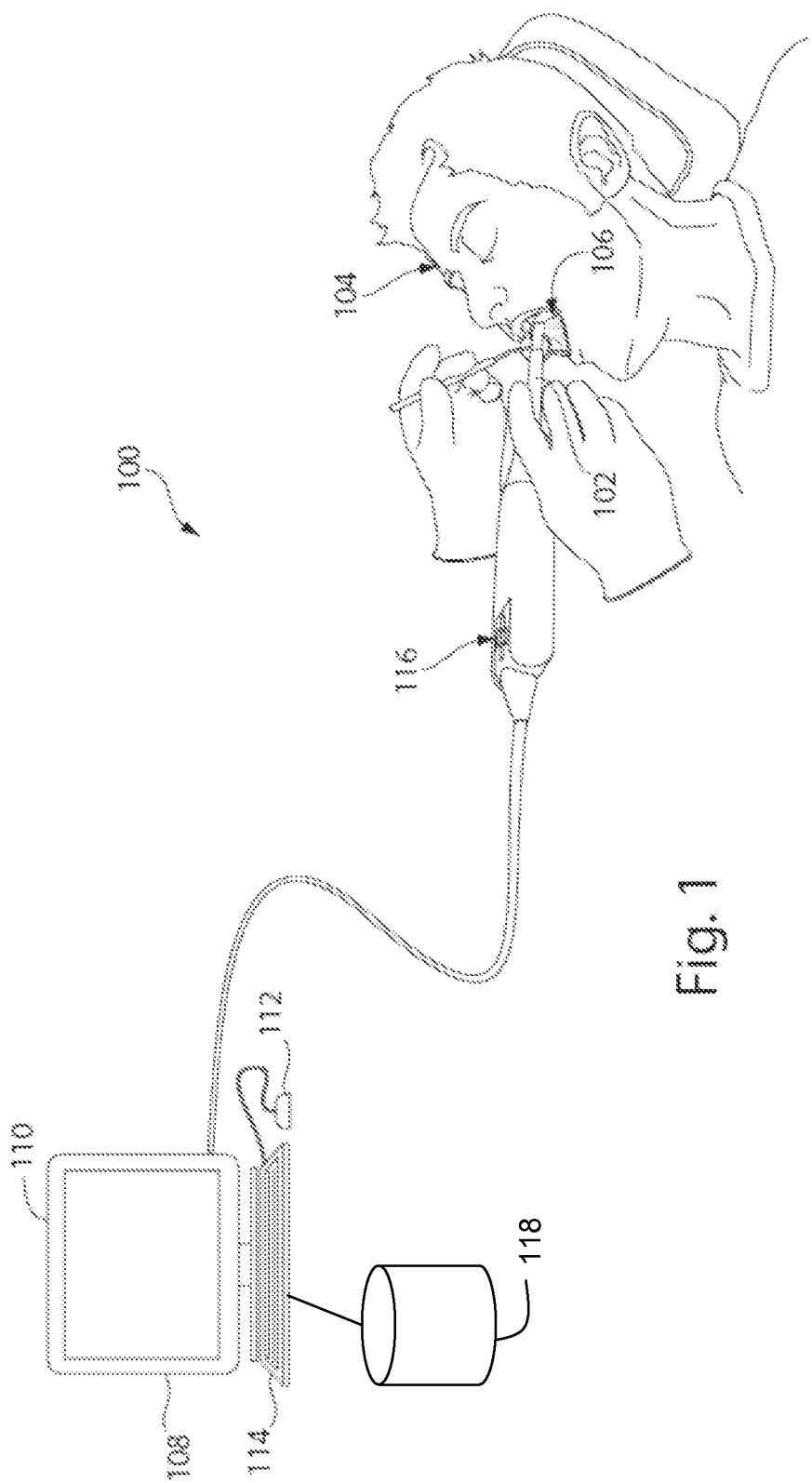
FIG. 1 shows a three-dimensional scanning system.

In the following text, references to items in the singular should be understood to include items in the plural, and vice versa, unless explicitly stated otherwise or clear from the text. Grammatical conjunctions are intended to express any and all disjunctive and conjunctive combinations of conjoined clauses, sentences, words, and the like, unless otherwise stated or clear from the context.

The following description details specific scanning technologies and focuses on dental applications of three-dimensional imaging; however, it will be appreciated that variations, adaptations, and combinations of the methods and systems below will be apparent to one of ordinary skill in the art. For example, while an image-based system is described, non-image based scanning techniques such as infrared time-of-flight techniques or structured light techniques using patterned projections may similarly employ reconstruction based on camera path that may benefit from the improvements described herein. Similarly, while the following description emphasizes a refinement using concurrent images from two offset channels of a multi-aperture camera, it will be understood that the techniques may be similarly applied to refine frame-to-frame data for a camera path of a multi-aperture camera, or different frames of data for a conventional camera. As another example, while digital dentistry is one useful application of the improved accuracy that results from the techniques described herein, the teachings of this disclosure may also usefully be employed to refine three-dimensional animation models, three-dimensional scans for machine vision applications, and so forth. All such variations, adaptations, and combinations are intended to fall within the scope of this disclosure.

In the following description, the term "image" generally refers to a two-dimensional set of pixels forming a two-dimensional view of a subject within an image plane. The term "image set" generally refers to a set of related two-dimensional images that might be resolved into three-dimensional data. The term "point cloud" generally refers to a three-dimensional set of points forming a three-dimensional view of the subject reconstructed from a number of two-dimensional images. In a three-dimensional image capture system, a number of such point clouds may also be registered and combined into an aggregate point cloud constructed from images captured by a moving camera. Thus it will be understood that pixels generally refer to two-dimensional data and points generally refer to three-dimensional data, unless another meaning is specifically indicated or clear from the context.

The terms "three-dimensional model", "three-dimensional surface representation", "digital surface representation", "three-dimensional surface map", and the like, as used herein, are intended to refer to any three-dimensional reconstruction of an object, such as a point cloud of surface data, a set of two-dimensional polygons, or any other data representing all or some of the surface of an object, as might be obtained through the capture and/or processing of three-dimensional scan data, unless a different meaning is explicitly provided or otherwise clear from the context. A "three-dimensional representation" may include any of the three-dimensional surface representations described above, as well as volumetric and other representations, unless a different meaning is explicitly provided or otherwise clear from the context.

In general, the terms "render" or "rendering" refer to a two-dimensional visualization of a three-dimensional object, such as for display on a monitor. However, it will be understood that a variety of three-dimensional rendering technologies exist, and may be usefully employed with the systems and methods disclosed herein. For example, the systems and methods described herein may usefully employ a holographic display, an autostereoscopic display, an anaglyph display, a head-mounted stereo display, or any other two-dimensional and/or three-dimensional display. As such, rendering as described herein should be interpreted broadly unless a narrower meaning is explicitly provided or otherwise clear from the context.

The term "dental object", as used herein, is intended to refer broadly to subject matter related to dentistry. This may include intraoral structures such as dentition, and more typically human dentition, such as individual teeth, quadrants, full arches, pairs of arches (which may be separate or in occlusion of various types), soft tissue, and the like, as well bones and any other supporting or surrounding structures. As used herein, the term "intraoral structures" refers to both natural structures within a mouth as described above and artificial structures such as any of the dental objects described below that might be present in the mouth. Dental objects may include "restorations", which may be generally understood to include components that restore the structure or function of existing dentition, such as crowns, bridges, veneers, inlays, onlays, amalgams, composites, and various substructures such as copings and the like, as well as temporary restorations for use while a permanent restoration is being fabricated. Dental objects may also include a "prosthesis" that replaces dentition with removable or permanent structures, such as dentures, partial dentures, implants, retained dentures, and the like. Dental objects may also include "appliances" used to correct, align, or otherwise temporarily or permanently adjust dentition, such as removable orthodontic appliances, surgical stents, bruxism appliances, snore guards, indirect bracket placement appliances, and the like. Dental objects may also include "hardware" affixed to dentition for an extended period, such as implant fixtures, implant abutments, orthodontic brackets, and other orthodontic components. Dental objects may also include "interim components" of dental manufacture such as dental models (full and/or partial), wax-ups, investment molds, and the like, as well as trays, bases, dies, and other components employed in the fabrication of restorations, prostheses, and the like. Dental objects may also be categorized as natural dental objects such as the teeth, bone, and other intraoral structures described above or as artificial dental objects such as the restorations, prostheses, appliances, hardware, and interim components of dental manufacture as described above.

Terms such as "digital dental model", "digital dental impression" and the like, are intended to refer to three-dimensional representations of dental objects that may be used in various aspects of acquisition, analysis, prescription, and manufacture, unless a different meaning is otherwise provided or clear from the context. Terms such as "dental model" or "dental impression" are intended to refer to a physical model, such as a cast, printed, or otherwise fabricated physical instance of a dental object. Unless specified, the term "model", when used alone, may refer to either or both of a physical model and a digital model.

It will further be understood that terms such as "tool" or "control", when used to describe aspects of a user interface, are intended to refer generally to a variety of techniques that may be employed within a graphical user interface or other user interface to receive user input that stimulates or controls processing including without limitation drop-down lists, radio buttons, cursor and/or mouse actions (selections by point, selections by area, drag-and-drop operations, and so forth), check boxes, command lines, text input fields, messages and alerts, progress bars, and so forth. A tool or control may also include any physical hardware relating to the user input, such as a mouse, a keyboard, a display, a keypad, a track ball, and/or any other device that receives physical input from a user and converts the physical input into an input for use in a computerized system. Thus in the following description the terms "tool", "control" and the like should be broadly construed unless a more specific meaning is otherwise provided or clear from the context.

FIG. 1 depicts a three-dimensional scanning system that may be used with the systems and methods described herein. In general, the system 100 may include a camera 102 that captures images from a surface 106 of an object 104, such as a dental patient, and forwards the images to a computer 108, which may include a display 110 and one or more user-input devices 112, 114 such as a mouse 112 or a keyboard 114. The camera 102 may also include an integrated input or output device 116 such as a control input (e.g., button, touchpad, thumbwheel, etc.) or a display (e.g., LCD or LED display) to provide status information.

The camera 102 may include any camera or camera system suitable for capturing images from which a three-dimensional point cloud or other three-dimensional data may be recovered. For example, the camera 102 may employ a multi-aperture system as disclosed in U.S. Pat. No. 7,372,642 to Rohály et al., the entire content of which is incorporated herein by reference. While Rohály discloses one multi-aperture system, it will be appreciated that any multi-aperture system suitable for reconstructing a three-dimensional point cloud from a number of two-dimensional images may similarly be employed. In one multi-aperture embodiment, the camera 102 may include a plurality of apertures including a center aperture positioned along a center optical axis of a lens that provides a center channel for the camera 102, along with any associated imaging hardware. In such embodiments, the center channel may provide a conventional video image of the scanned subject matter, while a number of axially offset channels yield image sets containing disparity information that can be employed in three-dimensional reconstruction of a surface. In other embodiments, a separate video camera and/or channel may be provided to achieve the same result, i.e., a video of an object corresponding temporally to a three-dimensional scan of the object, preferably from the same perspective, or from a perspective having a fixed, known relationship to the perspective of the camera 102. The camera 102 may also, or instead, include a stereoscopic, triscopic or other multi-camera or other configuration in which a number of cameras or optical paths are maintained in fixed relation to one another to obtain two-dimensional images of an object from a number of different perspectives. The camera 102 may include suitable processing for deriving a three-dimensional point cloud from an image set or a number of image sets, or each two-dimensional image set may be transmitted to an external processor such as contained in the computer 108 described below. In other embodiments, the camera 102 may employ structured light, laser scanning, direct ranging, or any other technology suitable for acquiring three-dimensional data, or two-dimensional data that can be resolved into three-dimensional data. While the techniques described below can usefully employ video data acquired by a video-based three-dimensional scanning system, it will be understood that any other three-dimensional scanning system may be supplemented with a video acquisition system that captures suitable video data contemporaneously with, or otherwise synchronized with, the acquisition of three-dimensional data.

In one embodiment, the camera 102 is a handheld, freely-positionable probe having at least one user-input device 116, such as a button, a lever, a dial, a thumb wheel, a switch, or the like, for user control of the image capture system 100 such as starting and stopping scans. In an embodiment, the camera 102 may be shaped and sized for dental scanning More particularly, the camera 102 may be shaped and sized for intraoral scanning and data capture, such as by insertion into a mouth of an imaging subject and passing over an intraoral surface 106 at a suitable distance to acquire surface data from teeth, gums, and so forth. The camera 102 may, through such a continuous data acquisition process, capture a point cloud of surface data having sufficient spatial resolution and accuracy to prepare dental objects such as prosthetics, hardware, appliances, and the like therefrom, either directly or through a variety of intermediate processing steps. In other embodiments, surface data may be acquired from a dental model such as a dental prosthesis, to ensure proper fitting using a previous scan of corresponding dentition, such as a tooth surface prepared for the prosthesis.

Although not shown in FIG. 1, it will be appreciated that a number of supplemental lighting systems may be usefully employed during image capture. For example, environmental illumination may be enhanced with one or more spotlights illuminating the object 104 to speed image acquisition and improve depth of field (or spatial resolution depth). The camera 102 may also, or instead, include a strobe, a flash, or some other light source to supplement illumination of the object 104 during image acquisition.

The object 104 may be any object, collection of objects, portion of an object, or other subject matter. More particularly with respect to the dental techniques discussed herein, the object 104 may include human dentition captured intraorally from a dental patient's mouth. A scan may capture a three-dimensional representation of some or all of the dentition according to a particular purpose of the scan. Thus the scan may capture a digital model of a tooth, a quadrant of teeth, or a full collection of teeth including two opposing arches, as well as soft tissue or any other relevant intraoral structures. The scan may capture multiple representations, such as a tooth surface before and after preparation for a restoration. As will be noted below, this data may be employed for subsequent modeling such as designing a restoration or determining a margin line for same. During the scan, a center channel of the camera 102 or a separate video system may capture video of the dentition from the point of view of the camera 102. In other embodiments where, for example, a completed fabrication is being virtually test fitted to a surface preparation, the scan may include a dental prosthesis such as an inlay, a crown, or any other dental prosthesis, dental hardware, dental appliance, or the like. The object 104 may also, or instead, include a dental model, such as a plaster cast, a wax-up, an impression, or a negative impression of a tooth, teeth, soft tissue, or some combination of these.

The computer 108 may include, for example, a personal computer or other processing device. In one embodiment, the computer 108 includes a personal computer with a dual 2.8 GHz Opteron central processing unit, 2 gigabytes of random access memory, a TYAN Thunder K8WE motherboard, and a 250 gigabyte, 10,000 rpm hard drive. In one current embodiment, the system can be operated to capture more than five thousand points per image set in real time using the techniques described herein, and store an aggregated point cloud of several million points. Of course, this point cloud may be further processed to accommodate subsequent data handling, such as by decimating the point cloud data or generating a corresponding mesh of surface data. As used herein, the term "real time" means generally with no observable latency between processing and display. In a video-based scanning system, real time more specifically refers to processing within the time between frames of video data, which may vary according to specific video technologies between about fifteen frames per second and about thirty frames per second. More generally, processing capabilities of the computer 108 may vary according to the size of the object 104, the speed of image acquisition, and the desired spatial resolution of three-dimensional points. The computer 108 may also include peripheral devices such as a keyboard 114, display 110, and mouse 112 for user interaction with the camera system 100. The display 110 may be a touch screen display capable of receiving user input through direct, physical interaction with the display 110. In another aspect, the display may include an autostereoscopic display or the like capable of displaying stereo images.

Communications between the computer 108 and the camera 102 may use any suitable communications link including, for example, a wired connection or a wireless connection based upon, for example, IEEE 802.11 (also known as wireless Ethernet), BlueTooth, or any other suitable wireless standard using, e.g., a radio frequency, infrared, or other wireless communication medium. In medical imaging or other sensitive applications, wireless image transmission from the camera 102 to the computer 108 may be secured. The computer 108 may generate control signals to the camera 102 which, in addition to image acquisition commands, may include conventional camera controls such as focus or zoom.

In an example of general operation of a three-dimensional image capture system 100, the camera 102 may acquire two-dimensional image sets at a video rate while the camera 102 is passed over a surface of the subject. The two-dimensional image sets may be forwarded to the computer 108 for derivation of three-dimensional point clouds. The three-dimensional data for each newly acquired two-dimensional image set may be derived and fitted or "stitched" to existing three-dimensional data using a number of different techniques. Such a system may employ camera motion estimation to avoid the need for independent tracking of the position of the camera 102. One useful example of such a technique is described in commonly-owned U.S. application Ser. No. 11/270,135, filed on Nov. 9, 2005, the entire content of which is incorporated herein by reference. However, it will be appreciated that this example is not limiting, and that the principles described herein may be applied to a wide range of three-dimensional image capture systems.

The display 110 may include any display suitable for video or other rate rendering at a level of detail corresponding to the acquired data. Suitable displays include cathode ray tube displays, liquid crystal displays, light emitting diode displays and the like. In general, the display 110 may be operatively coupled to, and capable of receiving display signals from, the computer 108. This display may include a CRT or flat panel monitor, a three-dimensional display (such as an anaglyph display), an autostereoscopic three-dimensional display or any other suitable two-dimensional or three-dimensional rendering hardware. In some embodiments, the display may include a touch screen interface using, for example capacitive, resistive, or surface acoustic wave (also referred to as dispersive signal) touch screen technologies, or any other suitable technology for sensing physical interaction with the display 110.

The system 100 may include a computer-usable or computer-readable medium. The computer-usable medium 118 may include one or more memory chips (or other chips, such as a processor, that include memory), optical disks, magnetic disks or other magnetic media, and so forth. The computer-usable medium 118 may in various embodiments include removable memory (such as a USB device, tape drive, external hard drive, and so forth), remote storage (such as network attached storage), volatile or non-volatile computer memory, and so forth. The computer-usable medium 118 may contain computer-readable instructions for execution by the computer 108 to perform the various processes described herein. The computer-usable medium 118 may also, or instead, store data received from the camera 102, store a three-dimensional model of the object 104, store computer code for rendering and display, and so forth.

Figure 2:
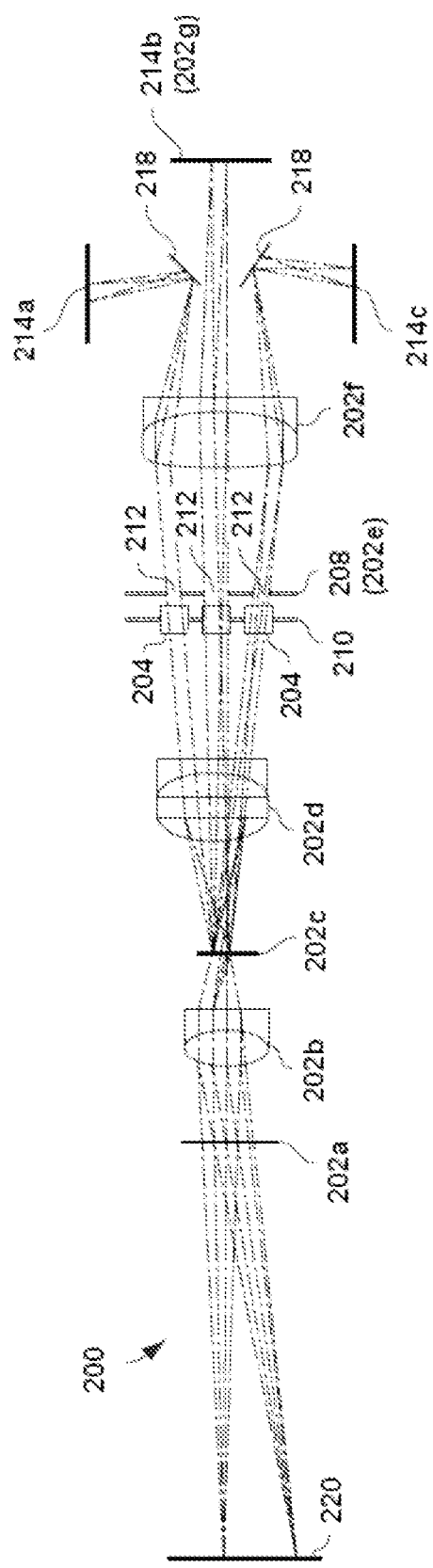
FIG. 2 shows a schematic diagram of an optical system for a three-dimensional camera.

FIG. 2 depicts an optical system 200 for a three-dimensional camera that may be used with the systems and methods described herein, such as for the camera 102 described above with reference to FIG. 1.

The optical system 200 may include a primary optical facility 202, which may be employed in any kind of image processing system. In general, a primary optical facility refers herein to an optical system having one optical channel. Typically, this optical channel shares at least one lens, and has a shared image plane within the optical system, although in the following description, variations to this may be explicitly described or otherwise clear from the context. The optical system 200 may include a single primary lens, a group of lenses, an object lens, mirror systems (including traditional mirrors, digital mirror systems, digital light processors, or the like), confocal mirrors, and any other optical facilities suitable for use with the systems described herein. The optical system 200 may be used, for example in a stereoscopic or other multiple image camera system. Other optical facilities may include holographic optical elements or the like. In various configurations, the primary optical facility 202 may include one or more lenses, such as an object lens (or group of lenses) 202*b*, a field lens 202*d*, a relay lens 202*f*, and so forth. The object lens 202*b* may be located at or near an entrance pupil 202*a* of the optical system 200. The field lens 202*d* may be located at or near a first image plane 202*c* of the optical system 200. The relay lens 202*f* may relay bundles of light rays within the optical system 200. The optical system 200 may further include components such as aperture elements 208 with one or more apertures 212, a refocusing facility 210 with one or more refocusing elements 204, one or more sampling facilities 218, and/or a number of sensors 214*a*, 214*b*, 214*c*.

The optical system 200 may be designed for active wavefront sampling, which should be understood to encompass any technique used to sample a series or collection of optical data from an object 220 or objects, including optical data used to help detect two-dimensional or three-dimensional characteristics of the object 220, using optical data to detect motion, using optical data for velocimetry or object tracking, or the like. Further details of an optical system that may be employed as the optical system 200 of FIG. 2 are provided in U.S. Pat. No. 7,372,642, the entire content of which is incorporated herein by reference. More generally, it will be understood that, while FIG. 2 depicts one embodiment of an optical system 200, numerous variations are possible. One salient feature of the optical system related to the discussion below is the use of a center optical channel that captures conventional video or still images at one of the sensors 214*b* concurrent with various offset data (at, e.g., 214*a* and 214*c*) used to capture three-dimensional measurements. This center channel image may be presented in a user interface to permit inspection, marking, and other manipulation by a user during a user session as describe below.

Figure 3:
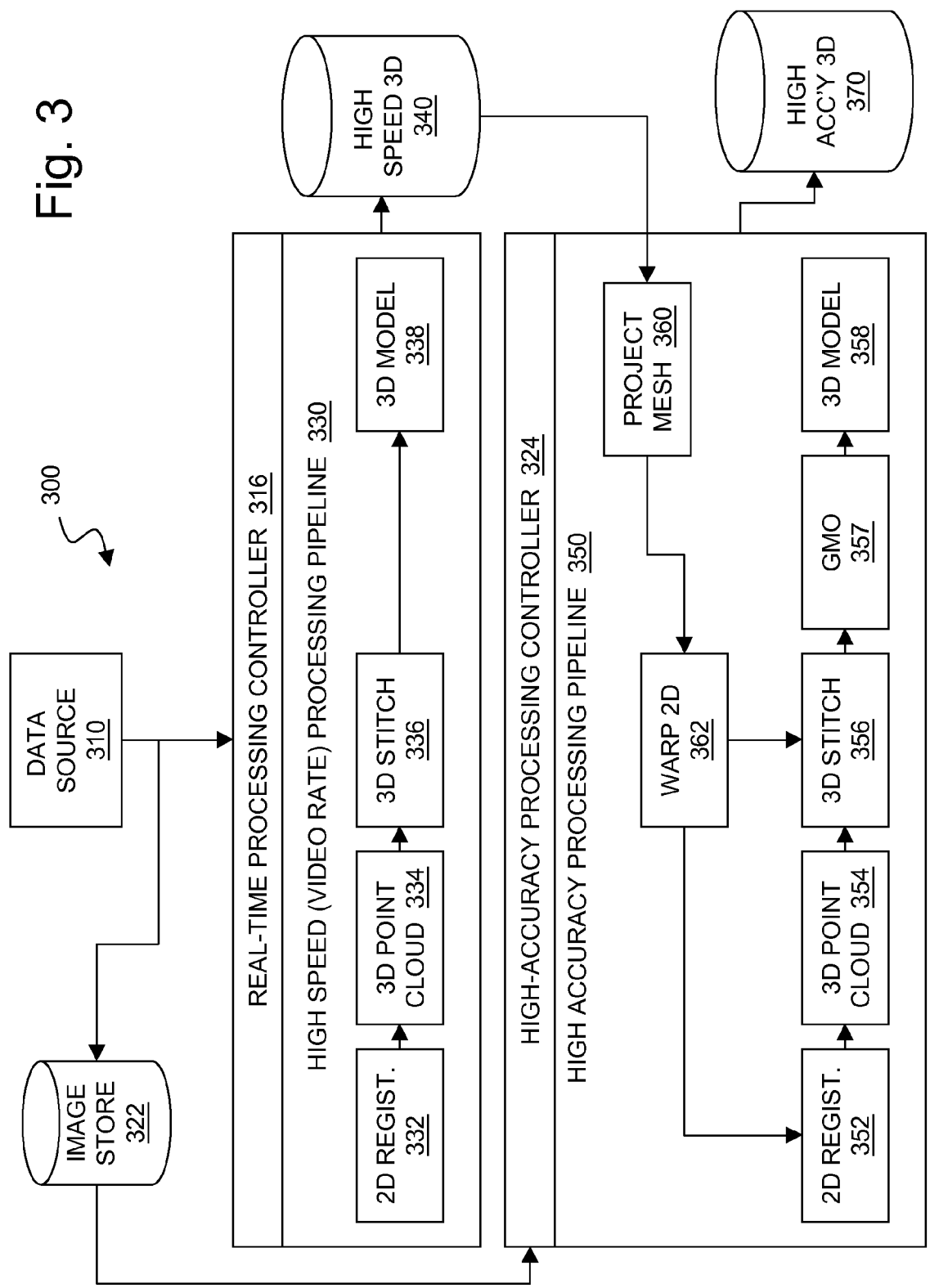
FIG. 3 shows a processing pipeline for obtaining three-dimensional data from a video camera.

FIG. 3 shows a three-dimensional reconstruction system 300 employing a high-speed pipeline and a high-accuracy pipeline. In general, the high-speed processing pipeline 330 aims to provide three-dimensional data in real time, such as at a video frame rate used by an associated display, while the high-accuracy processing pipeline 350 aims to provide the highest accuracy possible from camera measurements, subject to any external computation or time constraints imposed by system hardware or an intended use of the results. A data source 310 such as the camera 102 described above provides image data or the like to the system 300. The data source 310 may for example include hardware such as LED ring lights, wand sensors, a frame grabber, a computer, an operating system and any other suitable hardware and/or software for obtaining data used in a three-dimensional reconstruction. Images from the data source 310, such as center channel images containing conventional video images and side channels containing disparity data used to recover depth information may be passed to the real-time processing controller 316. The real-time processing controller 316 may also provide camera control information or other feedback to the data source 310 to be used in subsequent data acquisition or for specifying data already obtained in the data source 310 that is needed by the real-time processing controller 316. Full resolution images and related image data may be retained in a full resolution image store 322. The stored images may, for example, be provided to the high-accuracy processing controller 324 during processing, or be retained for image review by a human user during subsequent processing steps.

The real-time processing controller 316 may provide images or frames to the high-speed (video rate) processing pipeline 330 for reconstruction of three-dimensional surfaces from the two-dimensional source data in real time. In an exemplary embodiment, two-dimensional images from an image set such as side channel images, may be registered by a two-dimensional image registration module 332. Based on the results of the two-dimensional image registration, a three-dimensional point cloud generation module 334 may create a three-dimensional point cloud or other three-dimensional representation. The three-dimensional point clouds from individual image sets may be combined by a three-dimensional stitching module 336. Finally, the stitched measurements may be combined into an integrated three-dimensional model by a three-dimensional model creation module 338. The resulting model may be stored as a high-speed three-dimensional model 340.

The high-accuracy processing controller 324 may provide images or frames to the high-accuracy processing pipeline 350. Separate image sets may have two-dimensional image registration performed by a two-dimensional image registration module 352. Based on the results of the two-dimensional image registration a three-dimensional point cloud or other three-dimensional representation may be generated by a three-dimensional point cloud generation module 354. The three-dimensional point clouds from individual image sets may be connected using a three-dimensional stitching module 356. Global motion optimization, also referred to herein as global path optimization or global camera path optimization, may be performed by a global motion optimization module 357 in order to reduce errors in the resulting three-dimensional model 358. In general, the path of the camera as it obtains the image frames may be calculated as a part of the three-dimensional reconstruction process. In a post-processing refinement procedure, the calculation of camera path may be optimized—that is, the accumulation of errors along the length of the camera path may be minimized by supplemental frame-to-frame motion estimation with some or all of the global path information. Based on global information such as individual frames of data in the image store 322, the high-speed three-dimensional model 340, and intermediate results in the high-accuracy processing pipeline 350, the high-accuracy model 370 may be processed to reduce errors in the camera path and resulting artifacts in the reconstructed model. As a further refinement, a mesh may be projected onto the high-speed model by a mesh projection module 360. The resulting images may be warped or deformed by a warping module 362. Warped images may be utilized to ease alignment and stitching between images, such as by reducing the initial error in a motion estimation. The warped images may be provided to the two-dimensional image registration module 352. The feedback of the high-accuracy three-dimensional model 370 into the pipeline may be repeated until some metric is obtained, such as a stitching accuracy or a minimum error threshold.

Various aspects of the system 300 of FIG. 3 are described in greater detail below. In particular, a model refinement process is described that may be used by the high-accuracy processing controller 324 to refine the high accuracy three-dimensional model 370 using measured data in the image store 322. It should be understood that various processing modules, or the steps implied by the modules, shown in this figure are exemplary in nature and that the order of processing, or the steps of the processing sequence, may be modified, omitted, repeated, re-ordered, or supplemented, without departing from the scope of this disclosure.

Figure 4:
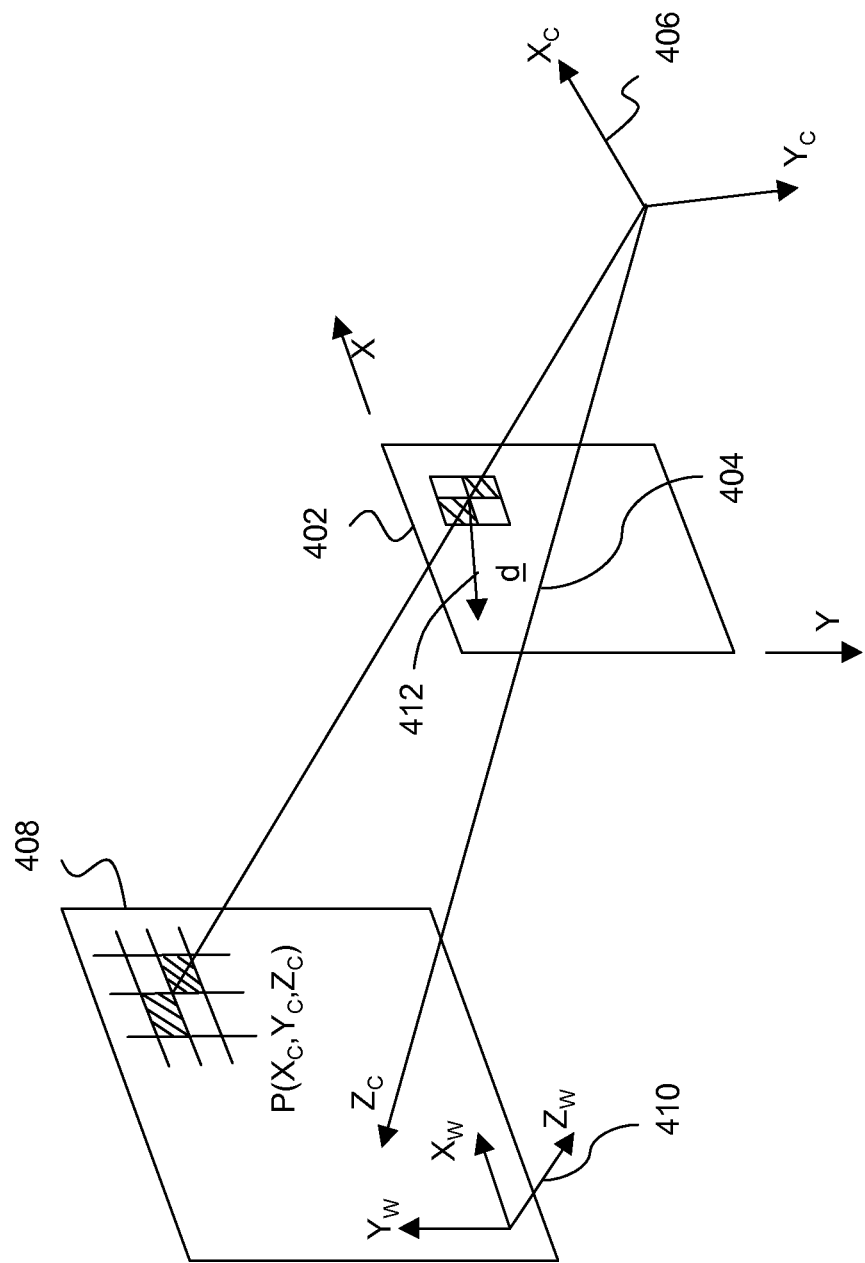
FIG. 4 illustrates a coordinate system for three-dimensional measurements.

FIG. 4 illustrates a coordinate system for three-dimensional measurements using a system such as the optical system 200 described above. The following description is intended to provide useful context, and should not be interpreted as limiting in any sense. In general an object 408 within an image plane 402 of a camera has world coordinates $\{X_w, Y_w, Z_w\}$ in a world coordinate system 410, camera coordinates $\{X_c, Y_c, Z_c\}$ n a camera coordinate system 406, and image set coordinates $\{x_i, y_i, d_i(x_i, y_i)\}$ for i=1 to N points or pixels within a processing mesh of the field of view 402, where $d_i$ is a disparity vector 412 containing one or more disparity values that characterize z-axis displacement ($Z_c$) or depth 404 of a point in the image plane 402 based upon x-axis and/or y-axis displacement in the image plane 402 between a number of physically offset apertures or other imaging channels. The processing mesh may be understood as any overlay or grid for an image or other two-dimensional data that identifies locations where processing will occur. While a processing mesh may be a regular grid of locations in a square, rectangular, triangular, or other pattern, the processing mesh may also, or instead, include irregular patterns selected randomly or according to the specific subject matter being processed. The disparity vector 412 may be expressed, for example, in terms of displacement relative to a center channel, if any, for the camera. In general, the disparity vector 412 encodes depth, and in various other three-dimensional imaging systems, this disparity vector 412 may be replaced by one or more other measured quantities that encode depth. Thus terms such as disparity vector, disparity value, and disparity data and the like should be understood broadly to include any one or more scalar and/or vector quantities measured by a system to capture depth information. Also more generally, a three-dimensional measurement as used herein may refer to any form of data encoding three-dimensional data including without limitation, groups of two dimensional images from which disparity vectors might be obtained, the disparity field (of disparity vectors) itself, or a three-dimensional surface reconstruction derived from the disparity field. In image-based three-dimensional reconstruction, a camera model may be employed to relate disparity vectors to depth within a field of view of a camera. The camera model may be determined theoretically based upon optical modeling or other physics, empirically through observation, or some combination of these, and may be calibrated to compensate for optical aberrations, lens defects, and any other physical variations or features of a particular physical system.

While a single image plane 402 is illustrated for purposes of explanation, it will be appreciated that a multi-aperture camera (or other multi-channel system) may have a number of physically offset optical channels that provide a different image plane for each channel, and the differences in feature locations (the x-y displacement) between the images for each optical channel may be represented as the disparity field. In various certain processing steps, the disparity data may be referenced to a single image plane such as a center channel image plane of the camera.

Figure 5:
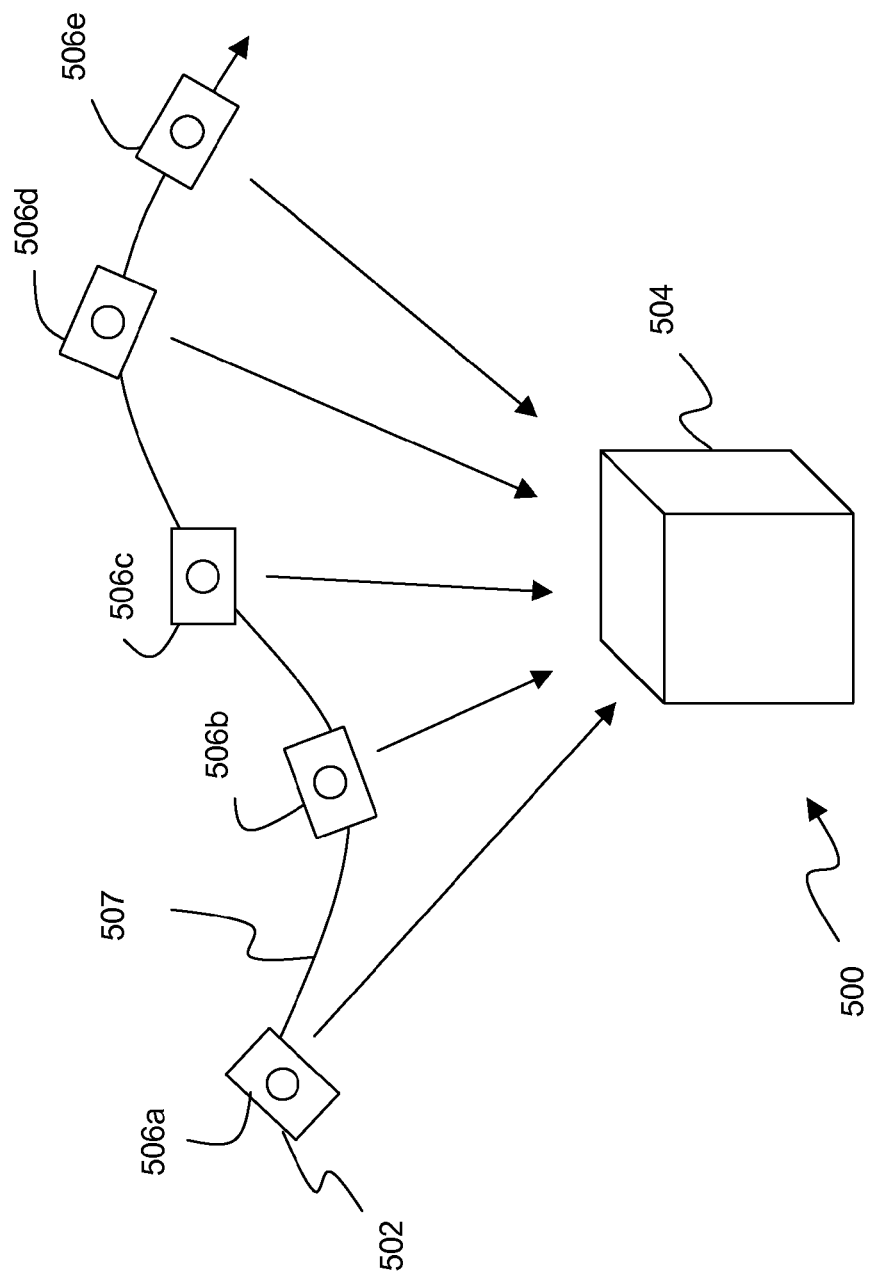
FIG. 5 illustrates a sequence of images captured from a moving camera.

FIG. 5 illustrates a sequence of images captured from a moving camera. In the sequence 500, a camera 502, which may include, for example, any of the cameras 102 described above, may capture an image of an object 504 from a number of different positions 506a-506e along a camera path 507. While the camera path 507 is depicted as a continuous curvilinear path which represents the physical path of a camera, it will be understood that analytically the camera path 507 may be represented by discrete, straight line transformations along with associated rotations in three-dimensional space. While five camera positions are shown in the camera path 507 of FIG. 5, it will be appreciated that more or fewer camera positions may be used consistent with the principles described herein. In an embodiment, the camera 502 may at each position 506 capture an image set:

$$ISn\{x_i+(x_i,y_i)^T|i+1,\ldots,N_n\} \quad [\text{Eq. 1}]$$

of two-dimensional images from which a point cloud:

$$PC_n\{X_i=(X_i,Y_i,Z_i)^T|i+1,\ldots,N_n\} \quad [\text{Eq. 2}]$$

may be reconstructed (or any other suitable three-dimensional measurement for the camera position). In general, these three-dimensional point clouds (or other three-dimensional data) captured from the sequence 500 may be combined into a three-dimensional model such as an aggregate point cloud or other three-dimensional model of the object, such as by minimization of errors in a three-dimensional registration of individual three-dimensional measurements, or any of a variety of other techniques. It should also be understood that, in certain embodiments, the camera may remain fixed while the subject moves. In such cases, motion of the object 504 is determined, rather than motion of the camera 502, although the use of camera motion versus object motion may be a relatively arbitrary matter of convenience, or of the computational efficiency of a camera coordinate system versus an object coordinate system.

Figure 6:
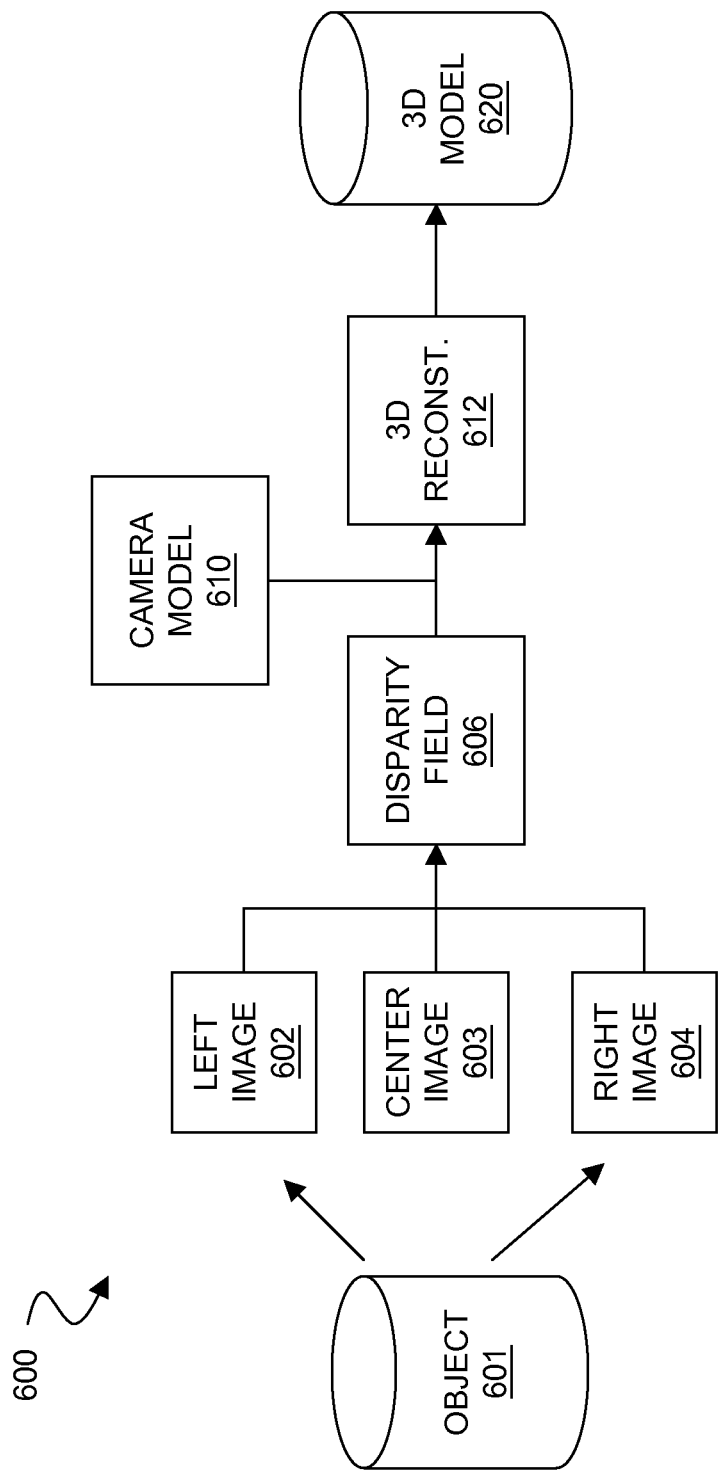
FIG. 6 is a conceptual representation of a three-dimensional data acquisition process.

FIG. 6 is a conceptual representation of a three-dimensional data acquisition process 600 that may be used in the systems described above. In general, the camera (which may be any of the cameras described above) obtains two-dimensional measurements of a surface of an object 601 such as a first measurement 602 from a side channel (e.g., a left channel image), a second measurement from another side channel 604 (e.g., a right channel image), and a third measurement from a center channel 603 (e.g., a center channel image). It will be understood that while three channels are depicted, a system may recover three-dimensional data from more or less channels using various techniques that will be apparent to one of ordinary skill, and any such techniques that might be improved with the refinement techniques described herein are intended to fall within the scope of this disclosure. These measurements 602, 603, 604 may be processed, for example, to obtain a disparity field 606 that identifies relative movement of features within the images of each measurement. A camera model 610 for the camera may be used to relate the disparity field 606 to the three-dimensional reconstruction 612 of the surface of the object 610 as measured from a camera pose. While a center channel image may conveniently be used as the reference for the camera pose of the resulting three-dimensional reconstruction 612, this is not required and may not, in certain systems be available as a reference in any event. The three-dimensional reconstruction 612 can be stitched to other such three-dimensional measurements using camera path information or the like to obtain a three-dimensional model 620 of the object 601.

In a model refinement process as described below, one of the two-dimensional measurements, such as the first measurement 602, may be projected onto the three-dimensional model using available spatial information (e.g., the camera position and orientation). The resulting projection may then be backprojected to the second camera pose using warping or other deformation techniques to obtain an expected measurement at the second camera position. In the case of a side channel two-dimensional image or the like, the expected measurement may be a corresponding image expected in the center channel or another side channel. By adapting the three-dimensional measurement from this image pair to reduce or minimize an error between the actual and expected measurements in an overlapping area of the object, the three-dimensional measurement may be refined for that camera position to more accurately represent a surface of the object 601. In one aspect, the three-dimensional model may be directly refined with the new spatial information. In another aspect, the improved three-dimensional measurement for the camera may be used in a new motion estimation to recover camera path and three-dimensional model data for an entire scan or any portion thereof. By refining the individual three-dimensional measurements and the camera path in this manner, a more accurate three-dimensional model for the object may be obtained. It will be appreciated that, in general, error minimization may be performed on a number of different data sets that encode three-dimensional information, such as the two-dimensional image sets, or upon processed representations of these measurement such as the disparity field.

Figure 7:
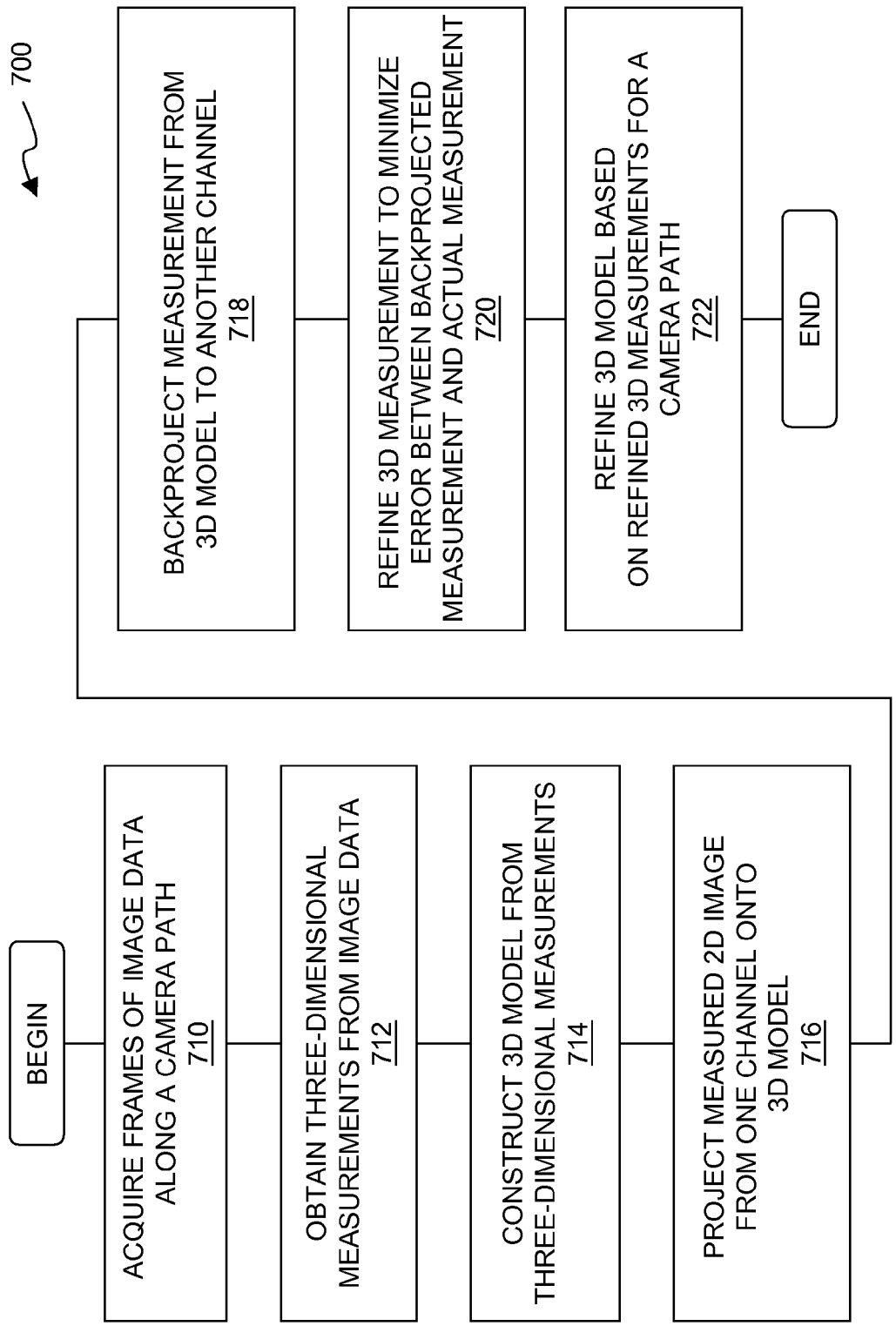
FIG. 7 is a flow chart of a process for refining three-dimensional data.

FIG. 7 is a flow chart of a process for refining three-dimensional data. In general, the process 700 refines a three-dimensional model by refining individual three-dimensional-measurements taken at different camera positions, which information may be employed to refine the resulting model. This process 700 may be usefully employed, for example, to warp two-dimensional images in a module 362 of a high accuracy processing pipeline 350, such as to improve two-dimensional registration and/or three-dimensional stitching results. While a particular embodiment is described below in detail, it will be appreciated that any similar technique for generating an expected two-dimensional measurement at one camera position using an actual two-dimensional measurement from a different camera position, along with a three-dimensional model of the imaged subject matter (and a camera model as appropriate), may similarly be employed. Thus the techniques described herein may be readily adapted to other systems that obtain a three-dimensional model from a series of individual three-dimensional measurements, such as systems using structured light or systems using a series of two-dimensional images.

As shown in step 710, the process 700 may begin by acquiring frames of image data along a camera path. This image data may include image pairs that capture an image from two or more offset optical channels of a multi-aperture camera or other multi-channel imaging device. In one embodiment, each image in an image pair contains a two-dimensional image from two coupled poses having a known, fixed relationship to one another. In such an embodiment, a center channel may also be provided that captures a third image as a part of the frame of image data to provide a conventional, undistorted two-dimensional view of the scanned subject matter (where distortions in the side channels encode distance to a surface). The center channel may also serve as a reference pose for a three-dimensional measurement derived from the pair of two-dimensional images. It will be understood, however, that this arrangement is somewhat arbitrary, and other cameras may be employed such as a camera with a center channel and a single side channel, or only two side channels, or any of a number of other arrangements. More generally, any camera that captures two-dimensional images for use in a three-dimensional reconstruction may be used with techniques described herein.

As shown in step 712, three-dimensional measurements may be obtained from the image data. In general, this may include processing image sets or the like to obtain disparity data across a processing mesh of the camera, and further processing the disparity data to obtain a three-dimensional surface reconstruction. In one embodiment, the disparity data encodes depth information, and may be employed to recover a three-dimensional measurement using a camera model or the like to relate disparity data to depth information for each pixel of the processing mesh. This step 712 may be repeated for each individual measurement (e.g., image set) obtained by the camera. As a result, a three-dimensional measurement or reconstruction may be obtained for each camera pose along a camera path. It will be understood that the disparity data is itself a three-dimensional measurement, and may be employed in place of a three-dimensional reconstruction for many of the processing steps described herein, with suitable adaptations being readily understood by one of ordinary skill in the art. It will further be understood that other three-dimensional imaging techniques are known and may be adapted to obtain three-dimensional measurements from an object surface.

As shown in step 714, a three-dimensional model may be constructed from the individual three-dimensional measurements obtained in step 712. Where the three-dimensional measurements of the surface of the object overlap, these three-dimensional measurements may be registered to one another using any of a variety of known techniques. As a result, the camera path from pose to pose may be recovered, and the three-dimensional measurements from each pose may be combined into a full three-dimensional model of scanned regions of the surface of the object.

As shown in step 716, a two-dimensional image or other measurement from one channel of a camera may be spatially projected onto the full three-dimensional model obtained in step 714. In general, the raw camera measurement includes a two-dimensional image of pixel values, which may be projected onto the three-dimensional model using texture mapping or any other suitable techniques to place the two-dimensional data from the image sets into the coordinate system of the three-dimensional model. As a significant advantage, this approach employs a three-dimensional model of the object that may, for example, contain global information that was not available when the data was initially collected. The model may, for example, average errors and/or reduce noise in individual camera measurements, as well as minimizing errors in a global camera path where possible. Using this initial model as a starting spatial reference point, the process 700 may revisit the individual three-dimensional measurements as further described below.

As shown in step 718, the projected measurement may be backprojected from the three-dimensional model to another channel of the camera, which may be the center channel or another side channel of the camera described above. The projected result from step 716 may be backprojected using any suitable techniques to obtain a synthetic view of the measurement from one camera channel as it should appear from the other camera channel, based upon the spatial relationship between the projected result, the three-dimensional model, and the position and rotation of the other channel. It will be appreciated that if there were no errors in the initial measurement, this synthetic view would exactly correspond to the actual two-dimensional image obtained from the other channel. However, in a high-speed processing pipeline such as that described above, an initial three-dimensional model may fail to accurately capture surface details for any number of reasons (lower resolution processing, absence of global surface data such as the completed three-dimensional model, etc.). Thus it is expected that in a practical system there may be variations between a synthesized view (based on observations from a different position) and an actual view. Backprojection may be accomplished, for example, by warping or otherwise deforming the projected result based upon the three-dimensional model and camera pose information for respective measurements. By processing these synthesized image sets to obtain disparity data, and further backprojecting the synthesized disparity data through the camera model, a backprojected result may be obtained that represents a synthesized or expected version of the three-dimensional measurement from the second camera position.

As shown in step 720, a three-dimensional measurement by a camera (e.g., the measurement derived from an image set in a frame of data) may be refined by adjusting the three-dimensional reconstruction to minimize an error between the backprojected result obtained in step 718 and an actual corresponding two-dimensional measurement captured in step 710. More generally, where two images contain measurements from an overlapping portion of the surface of the object, the backprojected (e.g., synthesized) measurement and the actual measurement may be directly compared. In one embodiment, camera calibration data and other information descriptive of the camera or the channels of the camera may be incorporated into the projection and/or backprojection in order to improve three-dimensional accuracy of the resulting three-dimensional measurement.

As shown in step 722, the three-dimensional model may be refined based upon the refined three-dimensional measurements for each frame of image data. A number of techniques may be employed to refine the model. In one aspect, the three-dimensional data for a refined three-dimensional measurement may be used to directly modify the three-dimensional model, e.g., by estimating the contribution of the changes in the refined three-dimensional measurement on the reconstruction process for the three-dimensional model. In another aspect, a new motion-based reconstruction for some or all of the scan data may be performed using the refined three-dimensional measurements in place of the initial three-dimensional measurements to recover a camera path used to relate the individual measurements to a global coordinate system. In another aspect, this process may be repeated to obtain iterative refinements in the three-dimensional model, e.g., for a predetermined number of iterations, or until a predetermined error threshold is reached, or until no further refinement is obtained from a previous iteration, and so forth, as well as various combinations of these. Iterations may be performed locally (e.g., on specific regions where errors are large) or globally (e.g., for every overlapping region between camera positions), or some combinations of these.

It will also be appreciated that this approach may be usefully employed with other three-dimensional reconstruction techniques, as well as in other ways within the image-pair based processing described above. For example, while the model-based refinement of a specific three-dimensional measurement may improve accuracy, the same approach may be employed to backproject a two-dimensional image from one image set onto a two-dimensional image from another image set in order to achieve frame-to-frame improvements in accuracy. Further, these image sets may be offset by any number of intervening image sets, and complementary, bi-directional refinements may be performed for any and all of the foregoing wherever the two measurements contain some overlap on the surface of the object. More generally, while a technique for testing a specific set of overlapping measurements is described above, this technique may be repeated any number of times, in any order, for some or all of the overlapping regions in measurements used to obtain a three-dimensional model, and all such variations are intended to fall within the scope of this disclosure.

Figure 8:
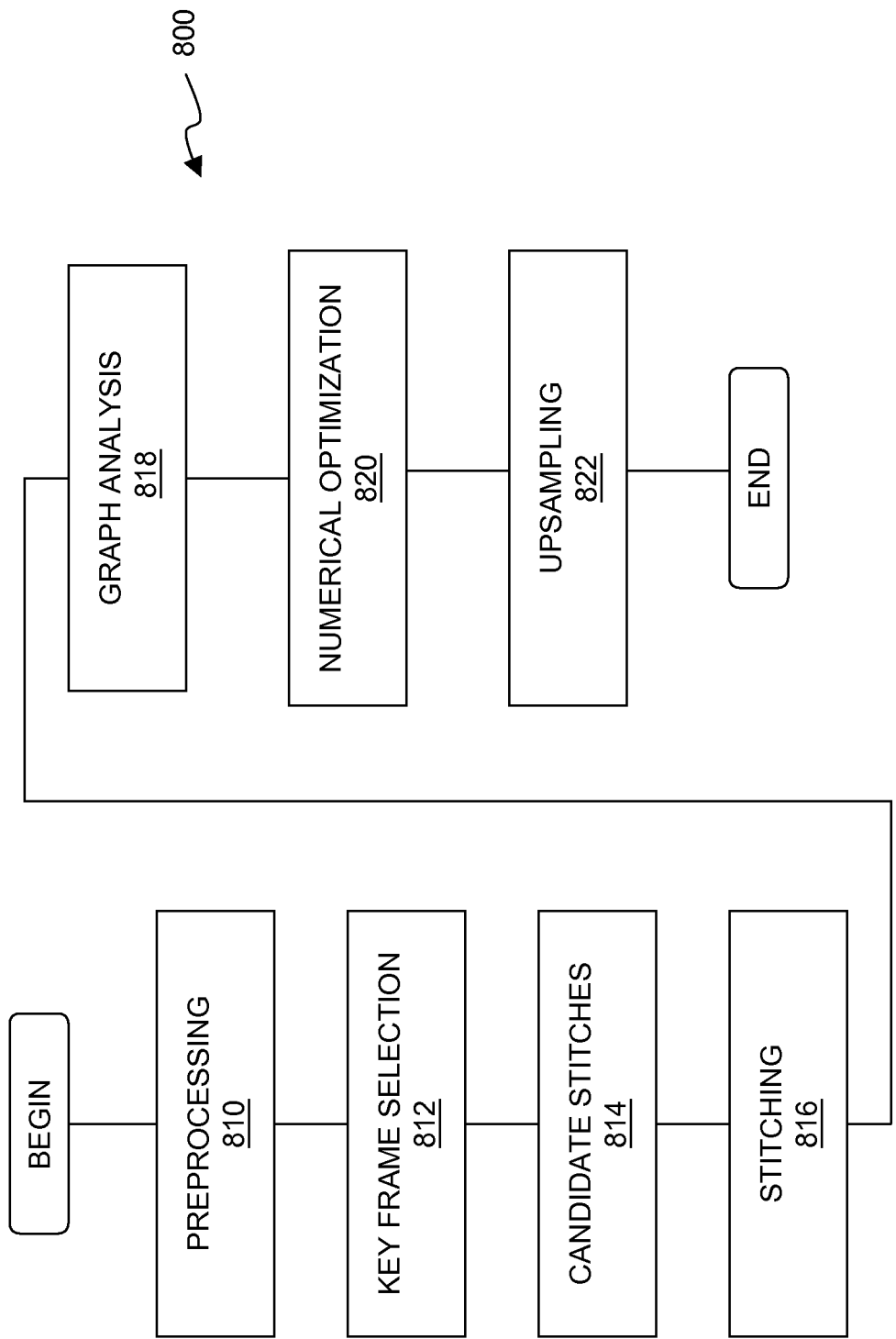
FIG. 8 is a flow chart of a global path optimization.

FIG. 8 is a flow chart of a global path optimization. In one aspect, the refinement of individual three-dimensional measurements may be used in combination with numerical techniques for global path optimization for an entire camera path to yield further iterative improvement to a resulting three-dimensional model. A suitable global path optimization technique is now described in greater detail.

The process 800 may begin with preprocessing as shown in step 810. It will be understood that preprocessing as described herein presupposes the availability of a number of frames of image data from which a camera path and three-dimensional model can be reconstructed. The information for the three-dimensional reconstruction may be generated in numerous ways including coming from structured light projection, shading based three-dimensional reconstruction, or disparity data. Disparity data may be generated by a conventional image plus one or more other channels or side channels. The preprocessing may include determining the number of available frames, the amount of overlap between neighboring frames, identification and elimination of frames with blurred or badly distorted images, and any other suitable preprocessing steps. An estimate of the number of desired key frames may be initially determined during the preprocessing step.

As shown in step 812, key frames may be selected from among all of the frames of data acquired from a scanner along a camera path. In general, computational costs can be reduced by storing certain data and performing certain calculations and processing steps exclusively with reference to key frames. These key frames may be related to one another in a manner that permits characterization of a complete camera path, typically through the registration of overlapping three-dimensional data in respective key frames. Various methods are known in the art for selecting a subset of frames of data as key frames, including techniques based on image overlap, camera path distance, the number of intervening non-key frames and so forth. Key frames may also or instead be selected based upon an amount of image overlap from the preceding key frame and/or a candidate for a following key frame (if available). Too little overlap may impair frame-to-frame registration. Too much overlap may produce excess key frames requiring additional processing. Key frames may be selected based on spatial displacement. Key frames may also be selected based on sequential displacement. This type of sequential displacement could mean for example that every tenth frame is selected as a key frame. In one aspect, key frames may be selected as data is acquired based on any number of suitable criteria. In another aspect, key frame pairs may be determined post hoc by examining all possible candidate key frames. All possible key frame pairs may be examined and candidates may be removed, for example, where there is insufficient overlap to form a stitch. Still more generally, any technique suitable for selecting a subset of frames in a data set may be usefully employed to select key frames for processing in order to reduce computational complexity.

Once key frames have been selected, additional processing may be performed. For example, full image data (e.g., full resolution center and side channel images) may be stored for each key frame, along with image signature data, point cloud centroid calculations, and any other measured or calculated data to support use of the key frames in a three-dimensional reconstruction process as described herein.

As shown in step 814, candidate stitches may be identified. In general, a stitch is a relationship between two separate three-dimensional measurements from two different camera poses. Once a stitch is established, a rotation and a translation may be determined for the path of a camera between the two poses. In a complementary fashion, the three-dimensional measurements from the poses may be combined into a portion of a three-dimensional model. Candidate stitches may be analyzed around each key frame, such as from the key frame to some or all of the frames of data between the key frame and neighboring key frames. In another aspect, a candidate stitch may be made to every other key frame, or in order to reduce computational complexity, every key frame within a spatial or sequential neighborhood around a key frame. Stitches may be based on the originally imaged frames. It may also be useful to deform or warp two-dimensional images during registration and other steps in a stitching process in order to improve accuracy and/or speed. Stitches may also or instead be based on other observed epipolar relationships in source data.

As shown in step 816, stitches may be selected for the complete camera path from the universe of candidate stitches. The selection of stitches may be made based upon, e.g., the lowest calculated error in resulting portions of the three-dimensional model. In general, each key frame may be stitched to one or more other key frames and each non-key frame may be stitched to at least one sequentially neighboring key frame.

As shown in step 818, a graph analysis may be performed using the key frames and the associated stitching to calculate a global path for the camera used to obtain a three-dimensional model. The graph analysis may consider each key frame as a node or vertex and each stitch as an edge between a pair of nodes. A key frame is selected as a starting point. A breadth- or depth-first search may be performed through the graph to identify stitches which may connect the current key frame to another key frame. Each key frame may be marked as the graph is processed. A check may be performed to see if all key frames have been reached within the graph. If all key frames have not been reached through traversing stitches in the graph analysis, the largest sub-graph is identified. This sub-graph may be examined to see if the entire three-dimensional image may be modeled.

It may be that certain sub-graphs are not required to complete the three-dimensional imaging. If the camera lingered over a particular region of a surface of an object, or if the camera looped on a region multiple times, the associated sub-graph(s) may not be needed. If a separate sub-graph is identified, which is needed to complete the three-dimensional imaging, an optional branch back to step 812 may be performed. For example, a set of key frames may have been selected which did not have sufficient stitching from one key frame to the next key frame. By choosing a different set of key frames, sufficient stitching may be obtained in order to obtain a complete graph of all needed aspects of the three-dimensional imaging. A key frame which is too sparse, meaning it has insufficient stitches to aid in building a graph, may indicate that a different set of key frames should be selected. Based on the graph analysis, a global path may be selected, and the graph may then be analyzed to optimize the path calculation.

As shown in step 820, a numerical optimization may be performed to reduce errors in the calculated camera path based upon available data for the complete camera path such as, for example, cross links that interrelate temporally distant measurements. In general, the objective of numerical optimization is to minimize a calculated error based upon an error function for the camera path and/or reconstructed three-dimensional model. A useful formulation of the error minimization problem for a global camera path is presented below.

There may be a set of candidate camera poses, each including a rotation and a translation (or position) referenced to a world coordinate system. There may also be a set of measured frame-to-frame camera motions, each including a rotation and a translation between poses. A measured camera motion may be referenced in the coordinate system of one camera pose. An example set of three key frames may be considered with an origin "O" and three other points "A", "B", and "C", each of the points having a position in a three-dimensional space. In addition to the position of these points, a camera at each of these points may have a different orientation. Therefore, between each of these points is a translation, meaning a change in position, and a rotation, meaning a change in orientation. The translation and rotation values comprise the motion parameters. The relationship between a point, X, expressed in the world coordinate system as $X_O$ and the same point expressed in the A coordinate system, $X_A$ may be expressed as:

$$X_A = R_{OA} X_O + T_{OA} \quad [\text{Eq. 3}]$$

$R_{OA}$ is the rotation taking points from the world to the A coordinate system. $T_{OA}$ is the translation of the world coordinate system to the A coordinate system. It should be understood that symbols X and T may represent a vector, rather than a scalar, e.g. where X includes x, y, and z coordinate values. Further, it should be understood that symbol R may represent a matrix. The following equations may similarly represent the transformation between the world and the B and C coordinate systems respectively:

$$X_B = R_{OB} X_O + T_{OB} \quad [\text{Eq. 4}]$$

$$X_C = R_{OC} X_O + T_{OC} \quad [\text{Eq. 5}]$$

By rearranging, equations 4 and 5 may be represented as follows:

$$X_O = R_{OA}^{-1}(X_A - T_{OA}) = R_{OB}^{-1}(X_B - T_{OB}) \quad [\text{Eq. 6}]$$

The representation of a point in one camera's coordinate system may be related to the same point in another coordinate system. For example, as in equations 3-5, coordinates of a point, X, may be transformed from the A coordinate system to the B coordinate system as follows:

$$X_B = R_{AB} X_A + T_{AB} \quad [\text{Eq. 7}]$$

The rotation $R_{AB}$ rotates points from the A to the B coordinate system and $T_{AB}$ translates the origin of the A coordinate system to the B coordinate system.

In optimization, the pose of every camera may be optimized based on measured transformations between poses. That is, a number of camera-to-world rotations and camera-to-world translations, $R_{On}$ and $T_{On}$ may be performed. In general, one of these may be defined as the identity rotation and zero translation, with the remaining values may be optimized as described below.

The rotations and translations may be measured for many pairs of cameras. For the ith such measured frame-to-frame motion, let one of the cameras of the pair be camera A and the other be camera B. This may also be considered the ith stitch. Let $R_{AB}^i$ be the measured rotation taking points in the A system to the B system and $T_{AB}^i$ be the coordinates of the A position expressed in the B system, as in equation 7.

The rotations and translations for all cameras, $R_{On}$ and $T_{On}$, may be optimized. $R_{C,OA}^i$ and $R_{C,OB}^i$ may be defined to be the candidate rotations; $T_{C,OA}^i$ and $T_{C,OB}^i$ may be defined to be the candidate translations corresponding to the A and B camera of the ith stitch. Further, $R_{C,AB}^i = R_{C,OB}^i (R_{C,OA}^i)^{-1}$ may be defined as the candidate rotation from A to B, and $T_{C,AB}{}^i = T_{C,OB}{}^i - R_{C,AB}{}^i T_{C,OA}{}^i$, the candidate translation for the transformation from A to B.

Note that with sufficient stitches, the motion constraints may form an overdetermined system of motion constraint equations. Using these equations as a starting point, numerical optimization may be performed on the rotational and translational components of each camera based on the measured stitches.

In a decoupled optimization, the rotational and translational components may be independently optimized. Given a candidate set of camera rotations, $R_C{}^i$ the corresponding candidate camera-to-camera rotations, $R_{C,AB}{}^i$ may be computed that correspond to each of the measured camera-to-camera rotations, $R_{AB}{}^i$. Thus the corresponding residual rotations are given by $R_{residual,AB}{}^i = R_{C,AB}{}^i (R_{AB}{}^i)^{-1}$. A scalar-valued rotational cost function, $e_r$, may be computed that depends on the candidate camera rotations $$e_r(R_{C,On}) = \sum_{i=1}^{\#stitches} r_r^{jT} r_r^j, \text{ where} \quad [\text{Eq. 8}]$$

$$r_r^j = \log_{SO(3)} R_{residual,AB}^i,$$

In equation 8, $\log_{SO(3)}(R)$ returns the axis-angle vector, v, that corresponds to the rotation R. In other words, $\log_{SO(3)}(R)$ returns the vector, v, that has a cross-product matrix, $[v]_x$, that is the matrix logarithm of R.

Next, a similar scalar-valued cost function may be computed for translation that depends on the candidate rotations and translations.

$$e_t(R_{C,On}, T_{C,On}) = \sum_{i=1}^{\#stitches} r_t^{jT} r_t^j, \text{ where} \quad [\text{Eq. 9}]$$

$$r_t^j = T_{C,AB}^i - T_{AB}^i$$

Equation 8 may be minimized as a nonlinear optimization; equation 9 may be minimized as a linear optimization.

In one conventional, decoupled approach to solving these simultaneous systems of equations, the rotational error function may be converted into a quaternion expression in order to translate the numerical problem into a linear system of equations for solution. While this approach may increase computational efficiency, it offers an incomplete optimization solution.

The decoupled approach described above does not provide a truly optimal one, in a maximum-likelihood sense, as it cannot use information from the translation portion of the stitches in determining rotation. In order to achieve a coupled optimization a weighting may be used to balance the contributions of rotational and translational components to a combined cost function:

$$e_c(R_{C,On}, T_{C,On}) = \sum_{i=1}^{\#stitches} \left( \begin{bmatrix} r_t^j \\ r_r^j \end{bmatrix}^T W_c^i \begin{bmatrix} r_t^j \\ r_r^j \end{bmatrix} \right) \quad [\text{Eq. 10}]$$

Multiple approaches may be used to optimize this cost function, but in one embodiment the weights may be expressed as matrices. Different stitches may receive different weightings based upon a number of factors including the number of points in the stitch (e.g., the shared content), the quality of a particular three-dimensional measurement, and/or any other factors impacting the known reliability of a stitch. In one approach, the weight matrices may also account for anisotropic error in the individual points collected, such as due to acquisition of depth information from disparity measurements, which results in measurement precision that varies with distance from the camera.

In some cases, equation 10 may be reformulated so that the rotation and translation weights are decoupled for each stitch (i.e., $W_c{}^i$ is a block diagonal). In particular, this may occur in the case where the motion stitches are recovered from three-dimensional point correspondences with isotropic point error. In that case, for a given stitch i, between camera A and camera B, the optimal solution may bring the point cloud as seen from camera A into correspondence with that seen from camera B. If $\bar{X}_A{}^i$ and $\bar{X}_B{}^i$ are the positions of the center of the point cloud in the A and B systems respectively, then $r_t{}^i$ may be replaced in equation 10 with the residual displacement between the point-cloud centers based on the candidate camera pose as follows:

$$r_{t,ctr}^i = \bar{X}_B^i - (R_{C,AB}^i \bar{X}_A^i + T_{C,AB}^i) \quad [\text{Eq. 11}]$$

Equation 10 may then be reformulated as:

$$e_c(R_{C,On}, T_{C,On}) = \sum_{i=1}^{\#stitches} \left( r_{t,ctr}^{iT} W_t^i r_{t,ctr}^i + r_r^{iT} W_r^i r_r^i \right) \quad [\text{Eq. 12}]$$

This coupled optimization problem may still be considered as being non-linear. It should be understood that other optimizations are also possible that would fall within the scope of this disclosure.

In general, by minimizing equation 10, both rotational errors and translational errors may be minimized simultaneously. The weight matrices can be chosen, for example, according to "First Order Error Propagation of the Procrustes Method for 3D Attitude Estimation" by Leo Dorst, IEEE Transactions on Pattern Analysis and Machine Intelligence, Vol. 27, No. 2, February 2005, pp. 221-9 which is incorporated in its entirety by reference. Once a more consistent set of motion parameters has been generated the three-dimensional model may be updated.

In one aspect, the residual error may be employed as a calibration metric. When total error or some portion of error has been minimized, the residual error may be evaluated. If a minimized error falls beyond a certain threshold then calibration for the scanner and associated hardware may be recommended, based upon an inference that the inability to produce better quality results is due to a miscalibration or other malfunction of the camera system. The threshold value may be empirically determined based on the specific scanner hardware equipment or it may be learned experientially over time for a given system. When a system is new or has been freshly aligned, expected minimized error values may be obtained. When minimized error values deviate from these expected values, a calibration state evaluation flag may be set, or other alert or message generated, indicating that the tool should be calibrated.

As shown in step 822, upsampling may be performed to augment a three-dimensional model with data from non-key frames. For example, non-key frames may be registered to nearby key frames to create small, local reconstruction patches including the full image detail available from non-key frames. In this manner, path optimization may be performed on a key-frame-based data set, thus reducing the data requiring processing, while retaining additional data points from non-key frames for use in the final three-dimensional model.

It will be appreciated that any of the above system and/or methods may be realized in hardware, software, or any combination of these suitable for the data acquisition and modeling technologies described herein. This includes realization in one or more microprocessors, microcontrollers, embedded microcontrollers, programmable digital signal processors or other programmable devices, along with internal and/or external memory. The may also, or instead, include one or more application specific integrated circuits, programmable gate arrays, programmable array logic components, or any other device or devices that may be configured to process electronic signals. It will further be appreciated that a realization may include computer executable code created using a structured programming language such as C, an object oriented programming language such as C++, or any other high-level or low-level programming language (including assembly languages, hardware description languages, and database programming languages and technologies) that may be stored, compiled or interpreted to run on one of the above devices, as well as heterogeneous combinations of processors, processor architectures, or combinations of different hardware and software. Thus in one aspect there is disclosed herein a computer program product comprising computer executable code that, when executing on one or more computing devices, performs any and/or all of the steps described above. At the same time, processing may be distributed across devices such as a camera and/or computer and/or fabrication facility and/or dental laboratory and/or server in a number of ways or all of the functionality may be integrated into a dedicated, standalone device. All such permutations and combinations are intended to fall within the scope of the present disclosure.

While the invention has been disclosed in connection with the preferred embodiments shown and described in detail, various modifications and improvements thereon will become readily apparent to those skilled in the art. Accordingly, the spirit and scope of the present invention is not to be limited by the foregoing examples, but is to be understood in the broadest sense allowable by law.

What is claimed is:

1. A method of refining a three-dimensional model comprising the steps of:
    providing a three-dimensional model of an object;
    obtaining a first two-dimensional image of the object from a first camera pose;
    obtaining a second two-dimensional image of the object from a second camera pose, wherein the second two-dimensional image includes a common portion of a surface of the object with the first two-dimensional image;
    projecting the first two-dimensional image onto the three-dimensional model, thereby providing a projected two-dimensional image;
    deforming the projected two-dimensional image based upon a spatial relationship of the first camera pose, the second camera pose, and the three-dimensional model to obtain an expected image from the second camera pose;
    comparing the second two-dimensional image to the expected image to identify one or more discrepancies; and
    correcting the three-dimensional model based upon the one or more discrepancies.

2. The method of claim 1 wherein the first camera pose and the second camera pose include a position and an orientation of a single camera in two dependent positions.

3. The method of claim 2 wherein the first camera pose and the second camera pose include a position and an orientation of two offset channels of a multi-aperture camera.

4. The method of claim 1 wherein the first camera pose and the second camera pose include a position and an orientation of a single camera in two independent positions.

5. The method of claim 4 wherein a relationship between the first camera pose and the second camera pose is calculated based upon a three-dimensional measurement of the surface of the object from each of the first camera pose and the second camera pose.

6. The method of claim 1 further comprising deriving the three-dimensional model from a plurality of three-dimensional measurements of the surface of the object from a plurality of camera poses including the first camera pose and the second camera pose.

7. The method of claim 1 further comprising applying the one or more discrepancies to directly refine the three-dimensional model.

8. The method of claim 1 further comprising applying the one or more discrepancies to refine a three-dimensional measurement from one or more of the first camera pose and the second camera pose to provide a refined measurement.

9. The method of claim 8 further comprising refining a camera path calculation for a camera path used to create the three-dimensional model using the refined measurement to provide a refined camera path.

10. The method of claim 9 further comprising using the refined camera path and the refined measurement to refine the three-dimensional model.

11. The method of claim 1 wherein the three-dimensional model includes a point cloud or a polygonal mesh.

12. A computer program product for refining a three-dimensional model of an object comprising computer executable code embodied on a computer readable medium that, when executing on one or more computing devices, performs the steps of:
    providing a three-dimensional model of an object;
    obtaining a first two-dimensional image of the object from a first camera pose;
    obtaining a second two-dimensional image of the object from a second camera pose, wherein the second two-dimensional image includes a common portion of a surface of the object with the first two-dimensional image;
    projecting the first two-dimensional image onto the three-dimensional model, thereby providing a projected image;
    deforming the projected image based upon a spatial relationship of the first camera pose, the second camera pose, and the three-dimensional model to obtain an expected image from the second camera pose;
    comparing the second two-dimensional image to the expected image to identify one or more discrepancies; and
    correcting the three-dimensional model based upon the one or more discrepancies.

13. The computer program product of claim 12 wherein the first camera pose and the second camera pose include a position and an orientation of a single camera in two dependent positions.

14. The computer program product of claim 13 wherein the first camera pose and the second camera pose include a position and an orientation of two offset channels of a multi-aperture camera.

15. The computer program product of claim 12 wherein the first camera pose and the second camera pose include a position and an orientation of a single camera in two independent positions.

16. The computer program product of claim 15 wherein a relationship between the first camera pose and the second camera pose is calculated based upon a three-dimensional measurement of the surface of the object from each of the first camera pose and the second camera pose.

17. The computer program product of claim 12 further comprising code for performing the step of deriving the three-dimensional model from a plurality of three-dimensional measurements of the surface of the object from a plurality of camera poses including the first camera pose and the second camera pose.

18. The computer program product of claim 12 further comprising code for performing the step of applying the one or more discrepancies to directly refine the three-dimensional model.

19. The computer program product of claim 12 further comprising code for performing the step of applying the one or more discrepancies to refine a three-dimensional measurement from one or more of the first camera pose and the second camera pose to provide a refined measurement.

20. The computer program product of claim 19 further comprising code for performing the step of refining a camera path calculation for a camera path used to create the three-dimensional model using the refined measurement to provide a refined camera path.

21. The computer program product of claim 20 further comprising code for performing the step of using the refined camera path and the refined measurement to refine the three-dimensional model.

22. The computer program product of claim 12 wherein the three-dimensional model includes a point cloud or a polygonal mesh.

* * * * *